United States Patent
Philpott

[19]

[11] Patent Number: 5,944,708
[45] Date of Patent: Aug. 31, 1999

[54] PROTECTIVE MENSTRUAL PANTY

[76] Inventor: Tracey Philpott, 401 9th Ct. West, Birmingham, Ala. 35204

[21] Appl. No.: 08/922,174

[22] Filed: Sep. 2, 1997

[51] Int. Cl.[6] .................................................. A61F 13/15
[52] U.S. Cl. ......................... 604/393; 604/394; 604/398; 2/406
[58] Field of Search .............................. 604/385.1, 385.2, 604/386, 392, 393, 394, 396–398; 2/406, 401

[56]  References Cited

U.S. PATENT DOCUMENTS

| | | | |
|---|---|---|---|
| 1,110,674 | 9/1914 | Rosiens | 607/398 |
| 1,924,642 | 4/1933 | Frieman | 604/391 |
| 2,102,359 | 12/1937 | Frieman | 604/397 |
| 2,165,561 | 7/1939 | Marcus | 604/397 |
| 2,954,770 | 10/1960 | Ruth | 604/396 |
| 4,022,212 | 5/1977 | Lovison . | |
| 4,560,381 | 12/1985 | Southwell . | |
| 4,690,681 | 9/1987 | Haunschild et al. . | |
| 4,813,950 | 3/1989 | Branch . | |
| 4,880,424 | 11/1989 | Rautenberg . | |
| 5,098,419 | 3/1992 | Gold . | |
| 5,277,130 | 1/1994 | Angellio et al. | 604/385.1 |
| 5,711,034 | 1/1998 | Cillik | 604/392 |

*Primary Examiner*—Mark O. Polutta
*Attorney, Agent, or Firm*—Michael I. Kroll

[57]  ABSTRACT

A protective menstrual panty (12) comprising a body portion (14) worn around a lower torso (16) of a female person (18) during menses. A liquid-proof elastic crotch portion (20) is provided. A facility (22) is for securing opposite ends (24) of the crotch portion (20) between front and rear lower segments (26), (28) of the body portion (14), so as to form two openings (30) for insertion of one of a pair of legs (32) of the female person (18) through each opening (30). A structure (34) is for holding a sanitary napkin (36) within the crotch portion (20) in a proper position, so that the sanitary napkin (36) will fit snugly against the inner thighs of the legs (32), and not tilt to leak from the sides thereof.

16 Claims, 4 Drawing Sheets

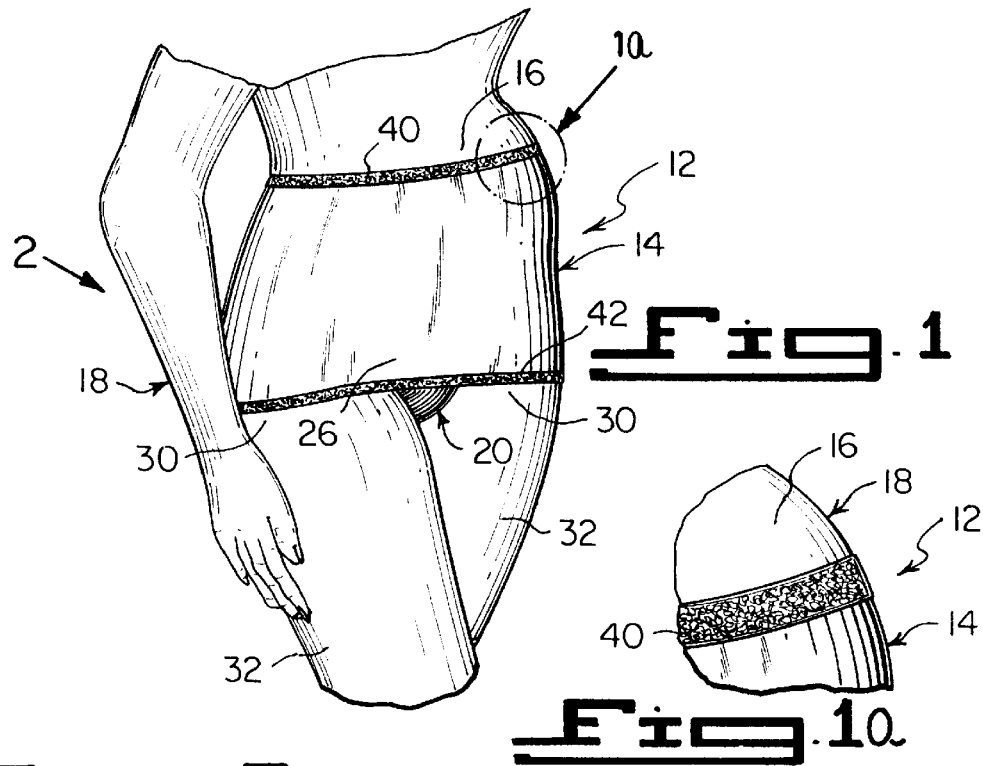
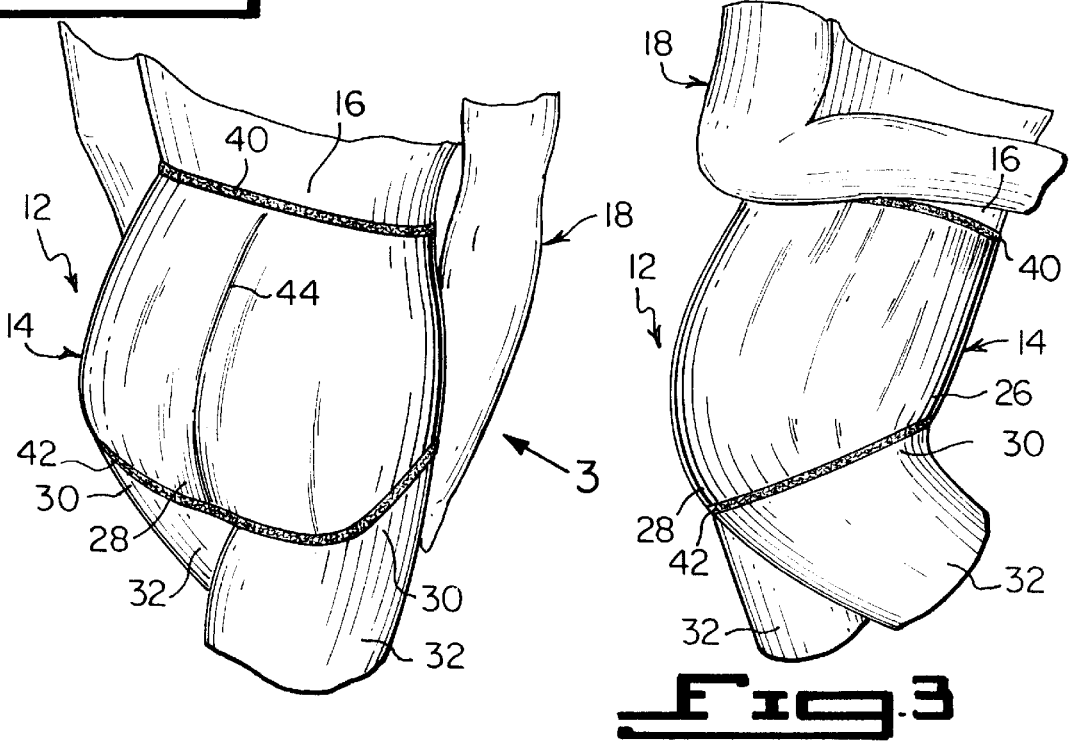

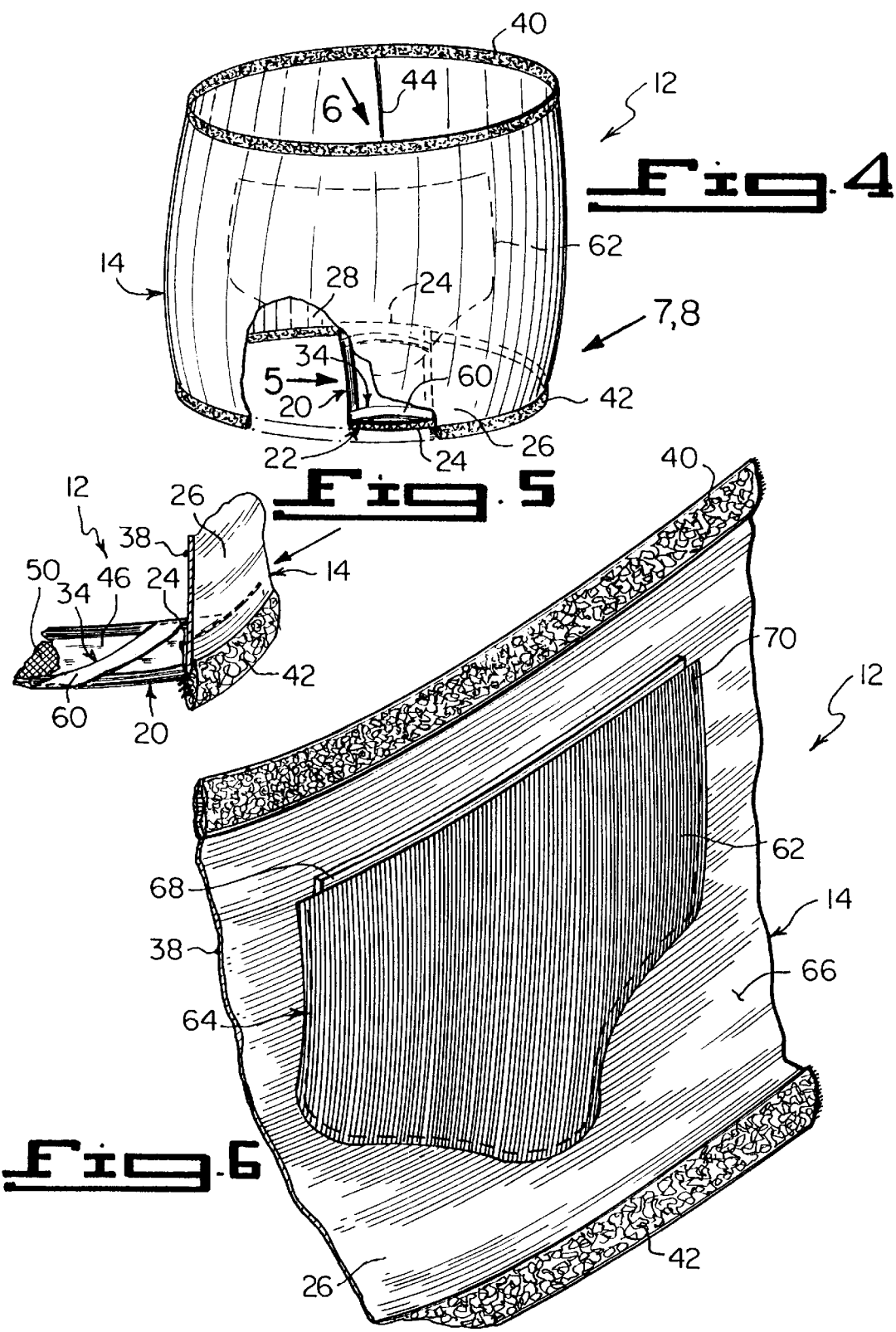

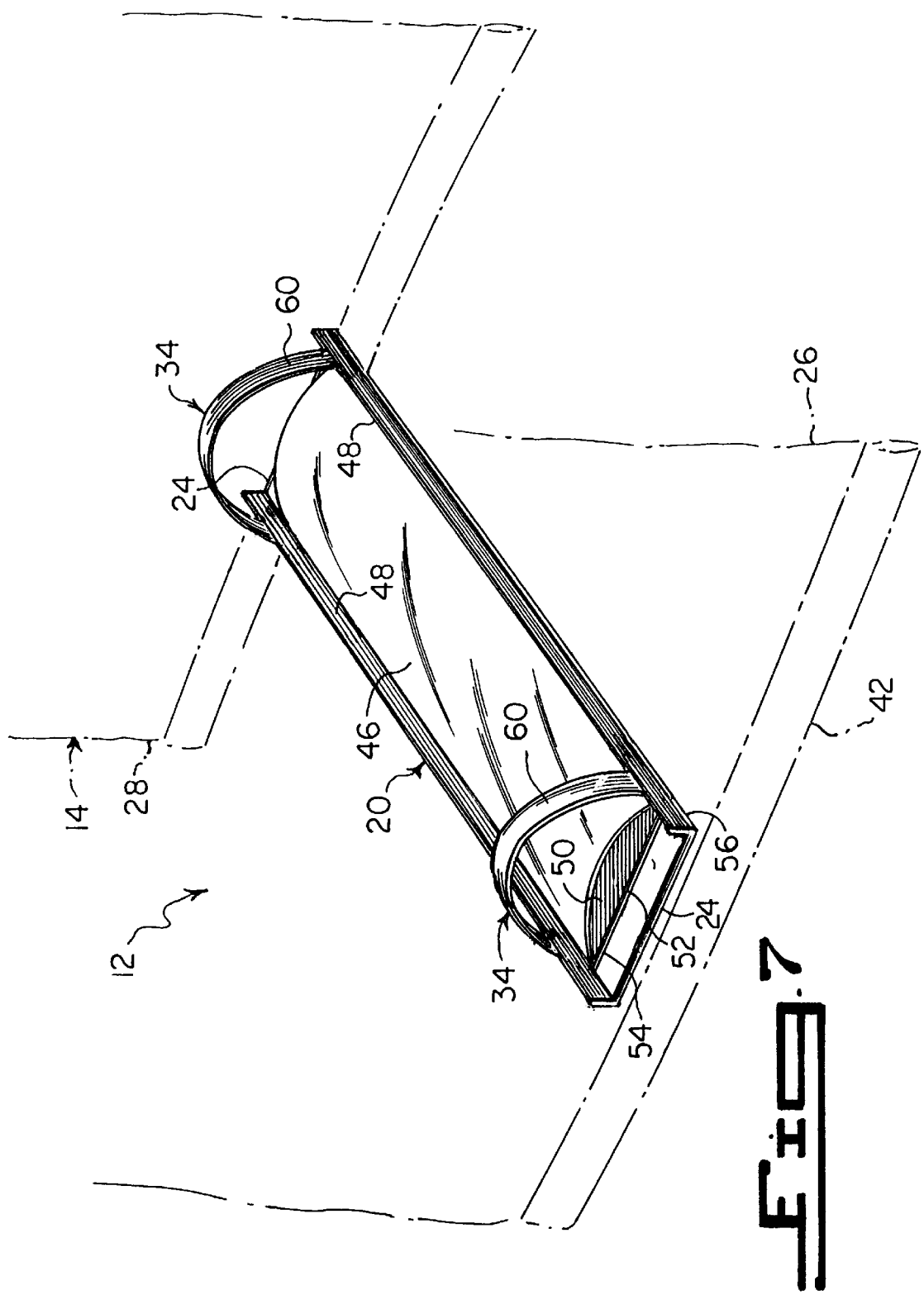

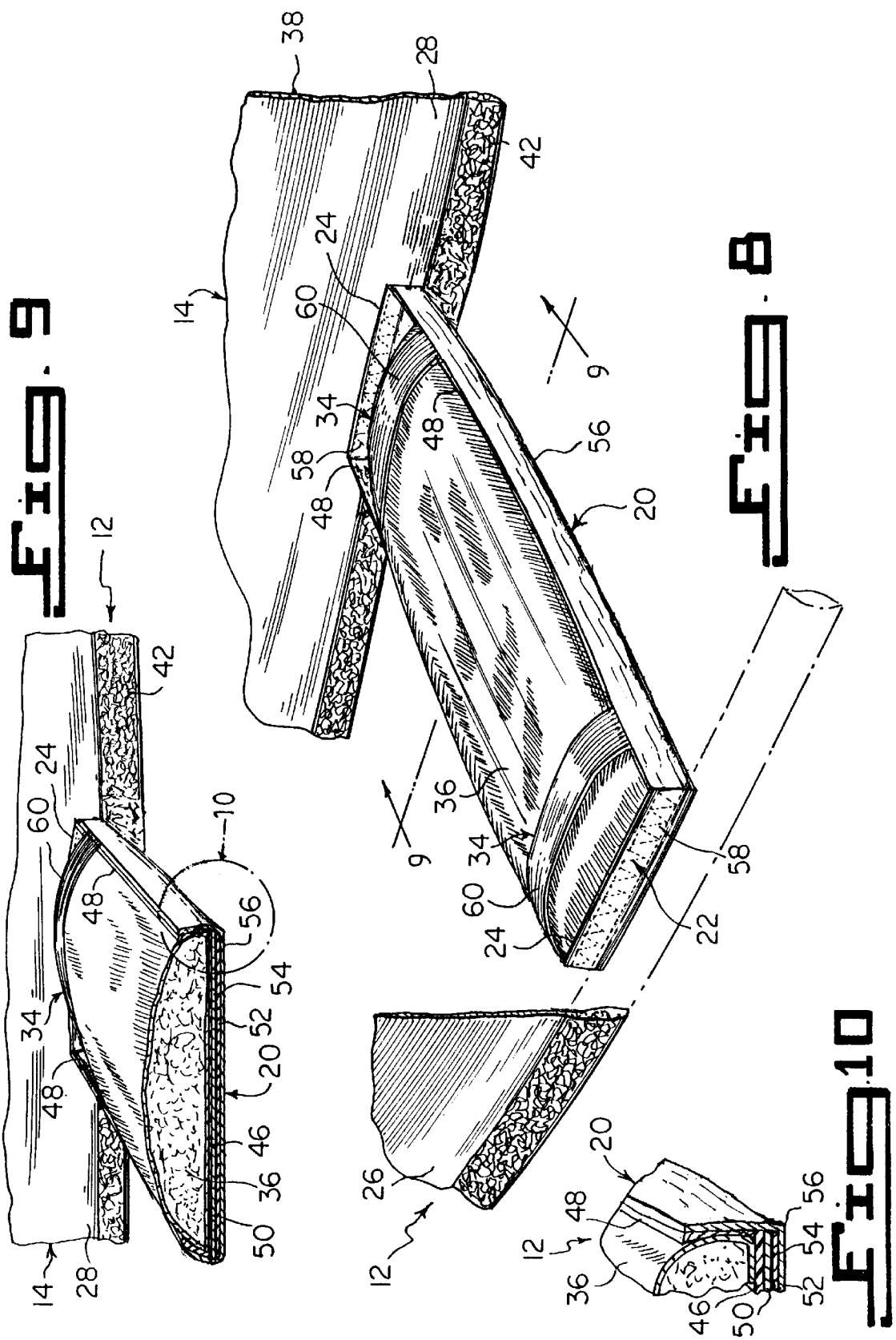

PROTECTIVE MENSTRUAL PANTY

BACKGROUND OF THE INVENTION

1. Field of the Invention

The instant invention relates generally to sanitary undergarments and more specifically it relates to a protective menstrual panty.

The protective menstrual panty fulfills a need for underwear to provide added comfort and increased protection against leakage for menstruating women. The appealing features of the protective menstrual panty is the increased protection it would offer against staining. By eliminating stains, embarrassment will be avoided. In addition, the panty will give a woman confidence, reassurance, and peace of mind that her underwear and outer wear would always be fresh and clean. The undergarment incorporates a number of features to secure a sanitary napkin in place. Furthermore, if leakage did occur, the crotch portion would disguise it due to it being produced in black. The protective menstrual panty will also be attractive and reasonably priced. The undergarment will also feature a body portion made from a stretchable fabric, which will flatten a bloated stomach. The present invention is versatile, in that, it can be used by women experiencing any type of discharge, such as the elderly who have bladder problems and women with yeast infections or bladder infections.

2. Description of the Prior Art

Although women have dealt with menstrual flow in many different ways throughout the ages, it wasn't until the early 1900s that they began to use cloth diapers and then surgical bandages to absorb the flow, which were then washed and used again or disposed of after use. After World War I, surplus bandage material was packaged as sanitary pads. The result was "KOTEX", the first successful disposable product for use during menstruation. "MODESS" pads came on the scene a few years later.

A whole new are of competition opened up in the 1930s with the invention of "TAMPEX"—an internal tampon with an applicator. Tampons were heralded as a revolutionary advance in hygiene and comfort. They were also denounced as an imminent threat to virginity and morality, a myth that faded with time. New brands of tampons, such as "PLAYTEX" and "KOTEX" were later introduced, and internal products steadily gained in popularity. Tampons without applicators, long popular in Europe, began to gain a following in the United States.

One of the most recent innovations in sanitary products cam in 1970. The conventional pad was reduced in size, stripped of its belt, and equipped with an adhesive band. The result was the mini-pad. Now available in several brands, mini-pads are promoted for use just before menstruation, on days of light flow, and as a supplement to tampons on days of heavy flow. They have been joined by larger versions known as maxi-pads, conventional-sized pads with an adhesive band for "beltless freedom."

More recently, sanitary napkins have undergone substantial reshaping. The trend, say Chris Ferdock, who manages the product for private label manufacturer Confab Cos., is toward much thinner, if longer, sanitary napkins. Highly absorbent materials have allowed for the emergency of ultrathin pads, which are suitable for heavy menstrual flow, but much less bulky than traditional sanitary maxipads. Johnson & Johnson's Personal Products Co., for example, claims that its new "STAYFREE ULTRA PLUS" is eighty percent thinner than regular maxipads. The key ingredient, say the company, is sphagnum, a type of moss harvested from bogs. By 1991, all of the major pad makers, Kimberly-Clark Corp., Procter & Gamble Co., and Johnson & Johnson had debuted ultrathin products—which, in less than a year, had grabbed a significant share of the market, drawing sales mainly from "THIN MAXIS". Ultimately, these new ultrathin pads could detract from sales of tampons.

Another recent innovation was the inclusion of decorative tote bags in boxes of pads that could also be used for proper and discreet disposal of the pads. One manufacturer of panty liners recently began offering a decorative box that is pretty enough to be placed in view on a dresser.

Even with all of the products available to make women more comfortable during menstruation, this is still often a very depressing time because by nature, the menstrual cycle has its up and downs due to hormonal changes. Only recently has the medical community recognized and labeled these changes as the Pre-Menstrual Syndrome (PMS), which affects an estimated twenty-five million American women. Symptoms of PMS can range from tension and irritability to cravings and stomach cramps. The most common symptoms are unexplained depression, anger, lethargy, unprovoked crying, and an inability to function normally. PMS is thought to account for an eight billion dollar loss each year through employee absenteeism.

The majority of American women, however, do not have major physical problems due to menstruation. But they often do have difficulties in coping with the menstrual flow. Most women are concerned about bleed-through, whether they are wearing a tampon or napkin. Despite all of the innovations to feminine hygiene products, women still experience leakage and stains on their expensive undergarments and outer wear. Not only could this be frustrating, but it could also be embarrassing. Some women spend a lot of time and money trying to soak underwear as well as pants, shorts and skirts in stain removers in an effort to save them from disposal. While this is often somewhat effective, the delicate fabrics used often cannot withstand the harsh chemicals used in these soaking solutions.

Numerous sanitary undergarments have been provided in prior art. For example, U.S. Pat. Nos. 4,022,212 to Lovison; 4,560,381 to Southwell; 4,690,681 to Haunschild et al.; 4,813,950 to Branch; 4,880,424 to Rautenberg and 5,098,419 to Gold all are illustrative of such prior art. While these units may be suitable for the particular purpose to which they address, they would not be as suitable for the purposes of the present invention as heretofore described.

Lovison, Paula J.

Hygienic Garment Assembly

U.S. Pat. No. 4,022,212

A hygienic garment assembly including a panty-type garment which is devoid of a crotch portion with the front and rear panels being cut off horizontally and hemmed, and a sanitary napkin which constitutes the crotch portion of the garment assembly, the ends of the napkin being fastened by detachable means to the hems of the front and rear panels, respectively.

Southwell, Sandra R. H.

Disposable Panty for Menstrual Wear

U.S. Pat. No. 4,560,381

The invention shows a protective, lightweight, disposable woman's hygienic panty for removably carrying a feminine napkin during a woman's menstrual cycle or period. A relatively thin, lightweight, disposable biodegradable, mesh-like outer panty shell is affixed to or contiguous with a relatively thick inner layer of absorbent material operably disposed about the inner surface of a lower body portion proximate at least the lower one half of the panty. Alternately, an inner shell or liner of relatively thick absorbent material having a pad-receiving depression can be fitted, temporarily or permanently, into ordinary menstrual panties or common panties or briefs. An elongated, nearly rectangular depression or indentation having oval end portions is included or formed in a relatively thick layer for carrying, aligning, or positioning a feminine napkin. The feminine napkin-shaped depression carries or positions the feminine napkin for use during the menstrual period and provides for easy removal when the napkin is soiled. The panty or liner may be discarded after a single use such as after a heavy discharge or several lightly soiled feminine napkins may be discarded before the entire panty or liner is thrown away. The invention contemplates a waist adjustable version and a one-size-fits-all version utilizing side slits and fasteners along the slits, to enable substantially all sizes of women to use a single protective panty in accordance with the present invention.

Haunschild, Susan M.

Hata, Stephen S.

Wismer, Shirlee A.

Disposable Leakproof Catamenial Device

U.S. Pat. No. 4,690,681

The invention is generally accomplished by providing a panty-like garment containing an integral menstrual pad. The absorbent pad portion extends from the crotch region up in both the back and the front to a point higher than normal menstrual pads. The pad extends at least up to the area where the crack between the gluteus maximus ends. Further there is an impervious member that is outside of the absorbent pad and greater in area than the absorbent pad.

Branch, Wilma J.

Sanitary Menses Panty

U.S. Pat. No. 4,813,950

A washable reusable sanitary panty designed to be worn during menses, normally occurring in non-pregnant women about every four weeks, from menarche to menopause. The sanitary panty is intended to be worn with a tampon or sanitary napkin, to prevent leakage and soiling of outer garments. The panty comprises a highly elastic woven or knit fiber outer covering configured in the shape of a panty and a contiguous non-women plastic film inner layer extending through the crotch, the inner layer being liquid water impermeable/water vapor permeable and of at least equal non-directional elasticity as the outer covering. In the preferred embodiment the panty is constructed of a spandex polyurethane fiber outer covering and a soft smooth microporous plastic film inner layer sewn to the outer layer. Both the outer and inner layer as well as the stitching are substantially unaffected by repeated washing and heated drying without the need for special care.

Rautenberg, Leonard J.

Protective Undergarment for the Retention of Body Fluids

U.S. Pat. No. 4,880,424

A garment to be worn on the lower part of the body for the retention of body fluids includes a body portion and a crotch portion. The body portion has a waist opening and the body and crotch portion form leg openings. A laminated fabric is disposed at least in the crotch portion for the retention of body fluids. The laminated fabric is liquid-proof, breathable and elastic. A preferred form of the laminated fabric includes a thermoplastic film layer and a fiber-containing material layer. The film layer is disposed inside the garment when the garment is worn.

Gold, David L.

Undergarment to be Worn by Incontinent Persons

U.S. Pat. No. 5,098,419

An undergarment that retains urine and other body fluids comprises an upper, or body, portion made of a knitted fabric, and a lower, or crotch, portion made of a woven, non-woven or knitted fabric. The crotch portion is coated with a modified polyester urethane polymer which prevents passage of body fluids, yet allows for some of the body condensate to escape by moisture vapor transmission. Because the crotch material is coated, rather than laminated, the garment body and crotch portion can be assembled without using special sewing needles, methods or speeds.

SUMMARY OF THE INVENTION

The protective menstrual panty incorporates various features to safeguard against leakage. The crotch section of the panty features elastic straps positioned at the front and back, which secures the sanitary napkin in place. In addition, the crotch section will be inside in the same length as the standard sanitary napkin, but slightly wider so that it will cradle the sanitary napkin. Furthermore, the crotch section will feature straight ends which will be attached to the front and back of the undergarment, to ensure the sanitary napkin will not move. This design will also ensure that the sanitary napkin will fit snugly against the inner thighs, so that it will not tilt, which can cause leakage. The use of the present invention will eliminate the embarrassment associated with the menstrual flow leaking through the individual's underwear and onto skirts, shorts, and pants. If leaking did occur, the black color of the crotch section will disguise it to reduce embarrassment.

The present invention also incorporates other features to provide the wearer with added comfort and peace of mind. The mid section of the undergarment features "LYCRA", which flattens a bloated stomach and enhances the wearer's shape. Furthermore, the seam of the protective menstrual panty rests in the center of the back panel to smooth lines, pull in the stomach area, and accentuate the shapeliness of the posterior.

A primary object of the present invention is to provide a protective menstrual panty that will overcome the shortcomings of the prior art devices.

Another object is to provide a protective menstrual panty that contains a crotch portion made of a LYCRA stretch material that is black in color to disguise any possible leakage therefrom.

An additional object is to provide a protective menstrual panty in which the crotch portion has two elastic bands placed near the front and back, to pull the sides of the crotch portion up to always keep a sanitary napkin centered on the crotch portion and fit snugly against the inner thighs, so that the sanitary napkin will not tilt to leak from the sides.

A further object is to provide a protective menstrual panty that is simple and easy to use.

A still further object is to provide a protective menstrual panty that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 1 is a front perspective view of the present invention worn on a lower trunk of a female person.

FIG. 1a is an enlarged perspective view of an area in FIG. 1, as indicated by arrow 1a.

FIG. 2 is a rear perspective view taken in the direction of arrow 2 in FIG. 1.

FIG. 3 is a side view taken in the direction of arrow 3 in FIG. 2.

FIG. 4 is a front perspective view of the present invention per se with parts broken away.

FIG. 5 is a side perspective view partly in cross section taken in the direction of arrow 5 in FIG. 4.

FIG. 6 is an inner perspective view taken in the direction of arrow 6 in FIG. 4, with parts broken away showing the thermal pouch and thermal insert in greater detail.

FIG. 7 is a perspective view taken in the direction of arrow 7 in FIG. 4, of the crotch portion with part of the body portion therebetween, shown in phantom.

FIG. 8 is a perspective view taken in the direction of arrow 8 in FIG. 4 of the crotch portion, with parts of the body portion therebetween broken away and the sanitary napkin held in place.

FIG. 9 is a cross sectional perspective view taken along line 9—9 in FIG. 8.

FIG. 10 is an enlarged cross sectional perspective view of an area in FIG. 9, as indicated by arrow 10.

Similar reference characters denote corresponding features consistently throughout the attached drawings.

DESCRIPTION OF THE PREFERRED EMBODIMENTS

Turning now descriptively to the drawings, in which similar reference characters denote similar elements throughout the several views, FIGS. 1 through 10 illustrate the present invention being a protective menstrual panty 12. With regards to the reference numerals used, the following numbering is used throughout the various drawing figures.

The protective menstrual panty 12 comprises a body portion 14 worn around a lower torso 16 of a female person 18 during menses. A liquid-proof elastic crotch portion 20 is provided. A facility 22 is for securing opposite ends 24 of the crotch portion 20 between front and rear lower segments 26, 28 of the body portion 14, so as to form two openings 30 for insertion of one of a pair of legs 32 of the female person 18 through each opening 30. A structure 34 is for holding a sanitary napkin 36 within the crotch portion 20 in a proper position, so that the sanitary napkin 36 will fit snugly against the inner thighs of the legs 32, and not tilt to leak from the sides thereof.

The body portion 14 is fabricated out of a soft stretch material 38. An elastic waistband 40 is attached about an open top end of the body portion 14, to keep the open top end in a snug fit about the waist of the female person 18. A soft stretch lace trim 42 is about an open bottom end of the body portion 14, to help keep the open bottom end of the body portion 14 to lie flat and give it a nice feminine look. The body portion 14 also includes a vertical central back seam 44, so as to smooth lines, pull in the stomach area and accentuate the shapeliness of the posterior of the female person 18.

The crotch portion 20 consists of a top sheet 46 made of black LYCRA material, to receive the sanitary napkin 36, where the potential area of leakage is located. A pair of side strips 48 made of black absorbent cotton material, are located on opposite sides of the top sheet 46. A side interface protective lining 50 is below the top sheet 46, to absorb potential wetness. A middle protective lining 52 stops the potential wetness. A liquid repellant 54 is coated on the bottom of the side interface protective lining 50. A bottom sheet 56 is made of black LYCRA material, so as to disguise any possible leakage therefrom.

The securing facility 22 includes thread stitches 58 sewn through the opposite ends 24 of the crotch portion 20 and front and rear lower segments 26, 28 of the body portion 14. The holding structure 34 consists of a pair of elastic retention straps 60. The elastic retention straps 60 are attached to opposite sides of the crotch portion 20 adjacent front and rear lower segments 26, 28 of the body portion 14, so as to keep the sanitary napkin 36 centered while pulling up the sides of the crotch portion 20 for a snug fit.

The protective menstrual panty 12, as shown in FIGS. 4 and 6, can further include a thermal pocket 62. A component 64 is for affixing the thermal pocket 62 to an inner surface 66 of the front segment 26 of the body portion 14. A thermal insert 68 fits into the thermal pocket 62, so as to help reduce a bloated stomach of the female person 18. The affixing component 64 includes thread stitches 70, sewn about side edges and bottom edge of the thermal pocket 62 and through the inner surface 66 of the front segment 26 of the body portion 14, while leaving the top edge open, so that the thermal insert 68 can be inserted within the thermal pocket 62.

Other features of the protective menstrual panty 12 includes the seam 44 which rests in the center of the back of the underwear. Furthermore, the mid-section is produced from a stretchable fabric 38 which will flatten a bloated stomach. In addition, it provides the female person 18 with a shapelier figure. The panty 12 would be available in small, medium, large and extra large sizes in bikini, full, and hip-hugger versions. The panty 12 could be produced in various colors with decorative appliques such as lace or bows and designs such as flowers.

The protective menstrual panty 12 will eliminate stains to expensive outer wear. Often, these stains can't be removed, and the clothing has to be discarded. A female person 18 will wear the protective menstrual panty 12 when she is experience a menstrual flow or other discharges without fear of ruining expensive clothing. The present invention could also be used by individuals with bladder control problems.

The potential exists for varying the production of the protective menstrual panty 12 in ways which could make it more appealing to a wider range of users. This could include offering bikini and brief versions with different leg cuts, as well as a variety of colors and decorative designs.

The protective menstrual panty 12 would represent a modification of an existing product, it would be readily producible. The protective menstrual panty 12 could be produced from a fabric such as cotton or nylon, with LYCRA for the mid section, which would be cut to size with power shears and sewn as desired. The elastic for the straps 60 in the crotch portion 20 would be readily available for inclusion within this product.

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A protective menstrual panty comprising:
   a) a body portion worn around a lower torso of a female person during menses;
   b) a liquid-proof elastic crotch portion including:
      i) a top sheet made of black LYCRA material, to receive the sanitary napkin, where potential area of leakage is located;
      ii) a pair of side strips made of black absorbent cotton material, located on opposite sides of said top sheet;
      iii) a side interface protective lining below said top sheet to absorb potential wetness;
      iv) a middle protective lining to stop the potential wetness;
      v) a liquid repellant coated on a bottom of said side interface protective lining; and
      vi) a bottom sheet made of black LYCRA material, so as to disguise any possible leakage therefrom;
   c) means for securing opposite ends of said crotch portion between front and rear lower segments of said body portion, so as to form two openings for insertion of one of a pair of legs of the female person through each opening; and
   d) means for holding a sanitary napkin within said crotch portion in a proper position, so that the sanitary napkin will fit snugly against the inner thighs of the legs, and not tilt to leak from the sides thereof.

2. The protective menstrual panty as recited in claim 1, wherein said body portion is fabricated out of a soft stretch material.

3. The protective menstrual panty as recited in claim 1, wherein said body portion includes an elastic waistband attached about an open top end to keep the open top end in a snug fit about the waist of the female person.

4. The protective menstrual panty as recited in claim 1, wherein said body portion includes a soft stretch lace trim about an open bottom end, to help keep the open bottom end of said body portion to lie flat and give it a nice feminine look.

5. The protective menstrual panty as recited in claim 1, wherein said body portion includes a vertical central back seam, so as to smooth lines, pull in the stomach area and accentuate the shapeliness of the posterior of the female person.

6. The protective menstrual panty as recited in claim 1, wherein said securing means includes thread stitches sewn through the opposite ends of said crotch portion and front and rear lower segments of said body portion.

7. The protective menstrual panty as recited in claim 1, wherein said holding means are a pair of elastic retention straps, in which said elastic retention straps are attached to opposite sides of said crotch portion adjacent front and rear lower segments of said body portion, so as to keep the sanitary napkin centered while pulling up the sides of said crotch portion for a snug fit.

8. The protective menstrual panty as recited in claim 1, further including:

a) a thermal pocket;

b) means for affixing said thermal pocket to an inner surface of said front segment of said body portion; and c) a thermal insert to fit into said thermal pocket, so as to help reduce a bloated stomach of the female person.

9. The protective menstrual panty as recited in claim 8, wherein said affixing means includes thread stitches, sewn about side edges and bottom edge of said thermal pocket and through the inner surface of said front segment of said body portion, while leaving the top edge open, so that said thermal insert can be inserted within said thermal pocket.

10. A protective menstrual panty as recited in claim 2, wherein said body portion includes an elastic waistband attached about an open top end to keep the open top end in a snug fit about the waist of the female person.

11. The protective menstrual panty as recited in claim 10, wherein said body portion includes a soft stretch lace trim about an open bottom end, to help keep the open bottom end of said body portion to lie flat and give it a nice feminine look.

12. The protective menstrual panty as recited in claim 11, wherein said body portion includes a vertical central back seam, so as to smooth lines, pull in the stomach area and accentuate the shapeliness of the posterior of the female person.

13. A protective menstrual panty as recited in claim 12, wherein said securing means includes thread stitches sewn through the opposite ends of said crotch portion and front and rear lower segments of said body portion.

14. The protective menstrual panty as recited in claim 13, wherein said holding means are a pair of elastic retention straps, in which said elastic retention straps are attached to opposite sides of said crotch portion adjacent front and rear lower segments of said body portion, so as to keep the sanitary napkin centered while pulling up the sides of said crotch portion for a snug fit.

15. The protective menstrual panty as recited in claim 14, further including:

a) a thermal pocket;

b) means for affixing said thermal pocket to an inner surface of said front segment of said body portion; and c) a thermal insert to fit into said thermal pocket, so as to help reduce a bloated stomach of the female person.

16. The protective menstrual panty as recited in claim 15, wherein said affixing means includes thread stitches, sewn about side edges and bottom edge of said thermal pocket and through the inner surface of said front segment of said body portion, while leaving the top edge open, so that said thermal insert can be inserted within said thermal pocket.

\* \* \* \* \*